United States Patent
Sekiguchi et al.

(10) Patent No.: US 7,244,620 B2
(45) Date of Patent: Jul. 17, 2007

(54) METHOD FOR QUANTITATIVELY DETERMINING A REDUCING SUBSTANCE AND A REAGENT FOR QUANTITATIVE DETERMINATION

(75) Inventors: Masahiro Sekiguchi, Ryugasaki (JP); Takuji Matsumoto, Ryugasaki (JP); Hiroyuki Ebinuma, Ryugasaki (JP)

(73) Assignee: Daiichi Pure Chemicals Co., Ltd., Tokyo (JP)

( * ) Notice: Subject to any disclaimer, the term of this patent is extended or adjusted under 35 U.S.C. 154(b) by 617 days.

(21) Appl. No.: 10/743,741

(22) Filed: Dec. 24, 2003

(65) Prior Publication Data

US 2005/0148089 A1 Jul. 7, 2005

(51) Int. Cl.
G01N 33/00 (2006.01)
G01N 21/00 (2006.01)
G01N 21/75 (2006.01)
C12Q 1/00 (2006.01)
C12P 11/00 (2006.01)
C12N 9/88 (2006.01)

(52) U.S. Cl. ............... 436/166; 436/119; 436/120; 436/164; 435/4; 435/130; 435/232

(58) Field of Classification Search ........ 436/119, 436/120, 164, 166; 435/4, 130, 232
See application file for complete search history.

(56) References Cited

U.S. PATENT DOCUMENTS 5,186,894 A 2/1993 Katsuyama
5,814,521 A * 9/1998 Chapoteau et al. ........... 436/74

FOREIGN PATENT DOCUMENTS

| EP | 1143244 A1 * | 10/2001 |
|---|---|---|
| JP | 4-157365 | 5/1992 |
| JP | 2000-166597 | 6/2000 |
| JP | 2000-270895 | 10/2000 |
| JP | 2000-338096 | 12/2000 |

OTHER PUBLICATIONS

H. Ozaki, et al., J. Biochem., vol. 91, No. 4, pp. 1163-1171, "Methionine Biosynthesis in Brevibacterium Flavum: Properties and Essential Role of O-Acetylhomoserine Sulfhydrylase", 1982.

S. Yamagata, J. Biochem., vol. 96, No. 5, pp. 1511-1523, "O-Acetylhomoserine Sulfhydrylase of the Fission Yeast Schizosaccharomyces Pombe: Parial Purification, Characterization, and its Probable Role in Homocysteine Biosynthesis", 1984.

J. Brzywczy, et al., Acta Biochimica Polonica, vol. 40, No. 3, "Comparative Studies on O-Acetylhomoserine Sulfhydrylase: Physiological Role and Characterization of the Aspergillus Nidulans Enzyme" 1993.

J. N. Burnell, et al., Biochimica el Biophysica Acta, vol. 481, pp. 246-265, "Sulphur Metabolism in Paracocus Denitrificans Purification, Properties and Regulation of Serine Transacetulase, O-Acetylsehine Sulphydrylase and β-Cystathionase" 1977.

T. Nagasawa, et al., Methods Enzymol, vol. 143, pp. 474-479, "O-Acetylserine Sulfhydrylase From *Bacillus sphaericus*", 1987.

M. Droux, et al., Archives of Biochemistry and Biophysics, vol. 295, No. 2, pp. 379-390, "Purification and Characterization of O-Acetylserine (Thiol) Lyase From Spinach Chloroplasts" Jun. 1992.

T. Yamaguchi, et al., BBA Biochimica et Biophysica Acta, vol. 1251, pp. 91-98, "Comparative Studies on Cysteine Synthase Isozymes From Spinach Leaves" 1995.

H. R. Hendrickson, et al., Method in Engymology, pp. 233-239, "β-Cyanoalanine Synthase (Blue Lupine)" vol. 17 Part B , 1971.

Tolosa, et al., Biochimiya, vol. 31, pp. 98-107, "Purification and Catalytic Properties of Cysteine Lyase From the Yolk Sac of Chicken Embryos", 1966 (with partial English translation).

* cited by examiner

*Primary Examiner*—Jill Warden
*Assistant Examiner*—Keri Moss
(74) *Attorney, Agent, or Firm*—Oblon, Spivak, McClelland, Maier & Neustadt, P.C.

(57) ABSTRACT

The present invention provides a method for quantitatively determining a reducing substance, which comprises reacting a reducing substance in a test specimen with iron (III) ions, reacting iron (II) ions formed by reduction of the iron (III) ions or residual iron (III) ions with a metal indicator which is capable of reacting specifically with the iron (II) ions or the residual iron (III) ions to undergo color development, and carrying out quantitative determination by measuring the degree of color development, wherein a chelating agent which is specific to copper ions is added to the test specimen before the reaction of the reducing substance with the iron (III) ions; and a reagent used for it.

17 Claims, No Drawings

METHOD FOR QUANTITATIVELY DETERMINING A REDUCING SUBSTANCE AND A REAGENT FOR QUANTITATIVE DETERMINATION

FIELD OF THE INVENTION

The present invention relates to a method wherein, when a reducing substance in a test specimen or a reducing substance formed from a component in a test specimen is quantitatively determined using iron ions and a metal indicator which is capable of reacting specifically with said iron ions to undergo color development, influence of a specific component coexisting in the test specimen can be avoided and the reducing substance originally existing or formed thereafter in the test specimen can be quantitatively determined with accuracy; and a reagent for such a quantitative determination.

BACKGROUND ART

As a method for quantitatively determining a reducing substance in a test specimen or a reducing substance formed by an enzyme reaction, etc. from a biological component in a biological specimen, methods wherein the reducing substance is reacted with iron (III) ions to reduce the iron (III) ions, and the formed iron (II) ions or residual iron (III) ions are detected/quantitatively determined with a metal indicator specific to these iron ions, have been known.

For example, a method wherein hydrogen sulfide or sulfide ions in a test specimen can be quantitatively determined conveniently with high sensitivity is disclosed in JP-A-2000-338096.

However, it was found that in the conventional methods, when a biological specimen such as serum or plasma and an environmental specimen such as sewage water or river water are the subject of measurement, accurate quantitative determination of the reducing substance might sometimes be difficult due to the influences of other components coexisting in the test specimen.

SUMMARY OF THE INVENTION

Accordingly, it is an object of the present invention to provide a method wherein, in a quantitative determination of a reducing substance in a test specimen by detecting iron (II) ions, which are formed by reacting the reducing substance with iron (III) ions, or residual iron (III) ions, using a metal indicator which is specific to the iron (II) ions or the residual iron (III) ions, influence by a specific component coexisting in the test specimen can be avoided to quantitatively determine the reducing substance accurately; and a reagent for such a quantitative determination.

In order to accomplish the above object, the present inventors have conducted extensive studies, and found out that copper ions, components containing copper, transferring, etc. coexisting in the test specimen, affect the measurement, and that the reducing substance in the test specimen can be quantitatively determined accurately by avoiding the influence of such components. The present invention has been made on the basis of this discovery.

The present invention provides a method for quantitatively determining a reducing substance, which comprises reacting a reducing substance in a test specimen with iron (III) ions, reacting iron (II) ions formed by reduction of the iron (III) ions or residual iron (III) ions with a metal indicator which is capable of reacting specifically with the iron (II) ions or the residual iron (III) ions to undergo color development, and carrying out quantitative determination by measuring the degree of color development, wherein a chelating agent which is specific to copper ions is added to the test specimen before the reaction of the reducing substance in the test specimen with the iron (III) ions. According to the present invention, by allowing the chelating agent specific to copper ions to coexist, it is possible to avoid the influence of copper ions and a component containing copper, whereby the reducing substance in the test specimen can be quantitatively determined accurately.

In the method for quantitatively determining a reducing substance of the present invention, the chelating agent which is specific to the copper ions is at least one selected from the group consisting of neocuproine, bathocuproine and salts thereof. According to this embodiment, influence of copper ions can be avoided without affecting the reaction of the iron ions with the metal indicator.

It is preferred to add at least one of an aluminum salt and a gallium salt to the test specimen. According to this embodiment, by allowing at least one of the aluminum salt and gallium salt to coexist, it is possible to avoid the influence of transferring, whereby the reducing substance in the test specimen can be quantitatively determined more accurately.

In the above embodiment, it is preferred to further add an organic acid to the test specimen together with at least one of an aluminum salt and a gallium salt. According to this embodiment, by allowing the organic acid to coexist, formation of hydroxides of aluminum and gallium in an alkaline pH range can be prevented, whereby it is possible to avoid influence of transferrins efficiently.

It is further preferred that the organic acid is tartaric acid. According to this embodiment, formation of hydroxides of aluminum and gallium can be prevented efficiently.

It is further preferred that the reducing substance is hydrogen sulfide or sulfide ions. According to this embodiment, the hydrogen sulfide or sulfide ions in the test specimen can be quantitatively determined accurately.

In this case, it is preferred that the hydrogen sulfide or sulfide ions are formed by reacting a sulfur-containing amino acid contained in the test specimen with an enzyme which is capable of reacting with the sulfur-containing amino acid to form hydrogen sulfide. According to this embodiment, by quantitatively determining the hydrogen sulfide or sulfide ions in the test specimen, a sulfur-containing amino acid such as homocysteine or cysteine in the test specimen can be quantitatively determined accurately.

It is preferred that the iron (III) ions constitute a complex. According to this embodiment, the stability of the iron (III) ions can be increased and the degree of color development of reagent blank can be reduced, whereby more accurate quantitative determination can be made.

In this case, it is preferred to add an auxiliary agent which has an ability of coordinating ligands around the iron ions to the test specimen together with the complex of the iron (III) ions. According to this embodiment, the iron (III) ions constituting a complex can be easily reduced by the reducing substance, whereby the measurement sensitivity can be improved.

It is further preferred that the test specimen is a biological specimen or an environmental specimen. According to this embodiment, influence of serum copper, transferrin and the like contained in the biological specimen such as serum, can be avoided, and influence of copper ions contained in the environmental specimen such as sewage water or river water can be avoided, whereby the reducing substance in the test specimen can be measured accurately.

The present invention also provides a reagent for quantitative determination of a reducing substance, which comprises a chelating agent which is specific to copper ions, iron (III) ions, and a metal indicator which is capable of reacting specifically with iron (II) ions or iron (III) ions to undergo color development. According to the present invention, it is possible to provide a reagent by which the reducing substance in a test specimen containing e.g. copper ions can be quantitatively determined conveniently and accurately.

In the reagent for quantitative determination of a reducing substance of the present invention, it is preferred that the chelating agent which is specific to copper ions is at least one selected from the group consisting of neocuproine, bathocuproine and salts thereof. According to this embodiment, influence of copper ions can be avoided without affecting the reaction of the iron ion with the metal indicator, whereby it is possible to provide a reagent suitable for quantitative determination of the reducing substance in an environmental specimen.

It is preferred that the reagent for quantitative determination of a reducing substance further comprises at least one of an aluminum salt and a gallium salt. According to this embodiment, influence of not only copper ions but also transferrins can be avoided, whereby it is possible to provide a reagent suitable for quantitative determination of a reducing substance in a biological specimen.

When at least one of an aluminum salt and a gallium salt is contained as above, it is preferred to further contain an organic acid. According to this embodiment, formation of hydroxides of aluminum and gallium in an alkaline pH range can be prevented, whereby it is possible to avoid influence of transferrins efficiently.

It is further preferred that the organic acid is tartaric acid. According to this embodiment, formation of hydroxides of aluminum and gallium can be prevented efficiently.

It is preferred that the reagent for quantitative determination of a reducing substance of the present invention, further comprises an enzyme which is capable of reacting with a sulfur-containing amino acid to form hydrogen sulfide. According to this embodiment, by quantitatively determining the hydrogen sulfide or sulfide ions in the test specimen, the sulfur-containing amino acid such as homocysteine or cysteine in the test specimen can be quantitatively determined accurately.

In the reagent for quantitative determination of a reducing substance of the present invention, it is preferred that the iron (III) ions constitute a complex. According to this embodiment, since the stability of the iron (III) ions is increased, which makes it is possible to improve the storage stability of the iron ion-containing reagent and to have iron ions and a metal indicator contained together in one reagent, whereby the number of reagents can be reduced. Further, the degree of color development of reagent blank can be reduced, and it is possible to obtain a reagent for quantitative determination by which quantitative determination can be made more accurately.

In the case where the complex of iron (III) ions is used, it is preferred that a reagent further comprises an auxiliary agent which has an ability of coordinating ligands around the iron ions. According to this embodiment, since the iron (III) ions constituting a complex is easily reduced by the reducing substance, it is possible to obtain a reagent for quantitative determination having a high sensitivity.

It is preferred that the reagent for quantitative determination of a reducing substance of the present invention is comprised of a first reagent containing the copper chelating agent and a second reagent containing the iron (III) ions and the metal indicator. According to this embodiment, by at first adding the first reagent to the test specimen, the copper ions contained in the specimen are chelated, and then by adding the second reagent, the reducing substance in the specimen is reacted with the iron (III) ions, whereby the influence of copper ions contained in the specimen or a component containing copper can securely be avoided and the reducing substance in the specimen can be quantitatively determined more accurately.

DETAILED DESCRIPTION OF THE INVENTION

The chelating agent which is specific to copper ions used in the present invention (hereinafter referred to as a copper chelating agent) is not particularly limited so far as it forms a complex with copper ions and does not adversely affect the reaction between iron (II) or iron (III) ions and a metal indicator which reacts specifically with them to undergo color development. For example, ones selected from neocuproine, bathocuproine and salts thereof may preferably be mentioned. More specifically, neocuproine hydrochloride, disodium bathocuproine disulfonate and the like may be mentioned. By using these copper chelating agents, influence of copper ions or a component containing copper can efficiently be avoided.

Further, the aluminum salt and the gallium salt used in the present invention are not particularly limited so far as they do not negatively affect the reaction between iron (II) or iron (III) ions and a metal indicator specific to them. As the aluminum salt, aluminum chloride, aluminum nitrate and the like may preferably be mentioned. As the gallium salt, gallium nitrate, gallium phosphate, gallium sulfate and the like may preferably be mentioned. The aluminum salt or gallium salt may be used alone or in combination. By using at least one of the aluminum salt and gallium salt, it is possible to avoid the influence of transferrins efficiently.

In the present invention, the test specimen is not particularly limited. The copper chelating agent may be used alone, or the copper chelating agent and at least one of the aluminum salt and the gallium salt may be used in combination, depending upon the type of other components contained in the test specimen. Specifically, when the test specimen contains copper ions or a component containing copper only, it is sufficient to use the copper chelating agent alone. Accordingly, for example, when an environmental specimen such as sewage water, river water, seawater or collected liquid from air is used, there is substantially no possibility that the specimen contains transferring, whereby influence of other components can be sufficiently avoided only by the copper chelating agent.

On the other hand, when copper ions, components containing copper, and transferring, are contained, it is preferred to use the copper chelating agent and at least one of the aluminum salt and the gallium salt in combination. Accordingly, when a biological specimen such as blood, serum or plasma is used, since serum copper (it is estimated that 90 to 95% of copper in the serum is bound to ceruloplasmin as one kind of serum protein, and the remains are bound to albumin) and transferrins are contained therein, it is preferred to use the copper chelating agent and at least one of the aluminum salt and the gallium salt in combination.

When at least one of the aluminum salt and the gallium salt is used, it is preferred to use an organic acid in combination in order to prevent formation of hydroxides of aluminum or gallium in an alkaline pH range. As the organic acid, tartaric acid, citric acid, malic acid, IDA (iminodiacetic acid) and the like may preferably be mentioned. Among them, tartaric acid and IDA are preferred, and tartaric acid is particularly preferred.

Further, the iron (III) ions are not particularly limited so far as they are liberated from a compound which liberates iron (III) ions in an aqueous solution (hereinafter referred to as iron (III) compound). For example, chelate compounds such as iron (III) monosodium ethylenediamine tetraacetate and iron (III) ammonium oxalate hydrate as well as ionic compounds such as iron (III) chloride, iron (III) sulfide ammonium hydrate, may be mentioned.

In the present invention, it is preferred that the iron (III) ions constitute a complex. As the complex of the iron (III) ions, for example, the above chelate compounds may preferably be used. Among them, iron (III) monosodium ethylenediamine tetraacetate may preferably be used. Further, the ionic compound of e.g. iron (III) chloride may be used under such condition that the iron (III) ions form a complex, for example, in the coexistence of a chelating agent such as ethylenediamine tetraacetate. By using a complex as the iron (III) ions, the stability of the iron ions can be improved, whereby the degree of color development of reagent blank can be reduced and the quantitative determination can be made more accurately.

Further, when the above complex is used, it is preferred that an auxiliary agent which has an ability of coordinating ligands around the iron ions (hereinafter referred to simply as an auxiliary agent) coexists in the test specimen. The auxiliary agent can appropriately be selected depending on the type of the iron (III) compound to be used. For example, IDA (iminodiacetic acid), ADA (N-(2-acetamide)iminodiacetic acid), Bicine (N,N-bis(2-hydroxyethyl)glycine), etc. may preferably be mentioned. Particularly preferred is ADA. By using the auxiliary agent, the iron (III) ions constituting a complex are readily reduced by a reducing substance, and the measurement sensitivity can be improved.

Further, as the metal indicator which is capable of reacting specifically with the iron (II) ions or the residual iron (III) ions to undergo color development, known metal indicators may be used, and the ones having a high sensitivity of color development are preferably used. In the explanation hereinbelow, the metal indicator which is capable of reacting specifically with the iron (II) ions to undergo color development is simply referred to as a metal indicator specific to iron (II) ions, and the metal indicator which is capable of reacting specifically with the iron (III) ions to undergo color development is simply referred to as a metal indicator specific to iron (III) ions. These are totally referred to as a metal indicator specific to iron ions.

As the metal indicator specific to iron (II) ions, for example, 1,10-phenanthroline hydrochloride, bathophenanthroline sulfonic acid, etc. as well as pyridylazo compounds, nitrosoaminophenol compounds, etc. may be used. Specifically, as the pyridylazo compounds, 2-(5-bromo-2-pyridylazo)-5-[N-n-propyl-N-(3-sulfopropyl)amino]phenol, disodium salt, dihydrate (tradename: 5-Br-PAPS, hereinafter abbreviated as 5-Br-PAPS), 2-(5-nitro-2-pyridylazo)-5-[N-n-propyl-N-(3-sulfopropyl)amino]phenol, disodium salt, dihydrate (tradename: Nitro-PAPS), etc. may preferably be mentioned. As the nitrosoaminophenol compounds, 2-nitroso-5-[N-n-propyl-N-(3-sulfopropyl)amino]phenol (tradename: Nitroso-PSAP), 2-nitroso-5-[N-ethyl-N-(3-sulfopropyl)amino]phenol (tradename: Nitroso-ESAP), etc. may preferably be mentioned.

As the metal indicator specific to iron (III) ions, for example, Feron, Calcichrome, Chromazurol B, Chromazurol S, Chromotropic acid, etc. may be mentioned. As the above metal indicators specific to iron ions, ones having various features are commercially available, and, for example, available from Dojindo Laboratories, etc.

In the quantitative determination method of the reducing substance of the present invention, the quantitative determination is feasible so far as the reducing substance is capable of reducing iron (III) ions. For example, ascorbic acid, hydrogen sulfide, sulfide ions, etc. may be mentioned. These are particularly suitable for the case where hydrogen sulfide or sulfide ions are quantitatively determined.

For example, with the above environmental specimen, hydrogen sulfide and sulfide ions are important index of environmental pollution, and the degree of environmental pollution can be judged by quantitatively determining them.

Further, with the above biological specimen, hydrogen sulfide or sulfide ions are formed when a sulfur-containing amino acid (homocysteine, cysteine, etc.) is reacted with an enzyme which is capable of reacting with the sulfur-containing amino acid to form hydrogen sulfide (hereinafter referred to as a hydrogen sulfide-producing enzyme), and by quantitatively determining them, the sulfur-containing amino acid can be quantitatively determined (JP-A-2000-166597 and JP-A-2000-270895). Homocysteine attracts attention as a risk factor of thromboembolism such as myocardial infarction or cerebral infarction, or arteriosclerosis. Cysteine may be an auxiliary index to grasp the cause of homocysteine metabolism disorder.

As the enzyme which reacts with homocysteine to form hydrogen sulfide, L-methionine-γ-lyase, o-acetylhomoserine-lyase, etc. may, for example, be mentioned. The L-methionine-γ-lyase is obtainable from, for example, microorganisms which are capable of producing it, such as bacteria of *pseudomonas* genus, etc. by a known method. Otherwise, ones commercially available from Wako Pure Chemical Industries, Ltd. may be used. Further, o-acetylhomoserine-lyase is obtainable from various microorganisms which are capable of producing it (for example, Ozaki et al., J. Biochem. 91; 1163-1171 (1982), Yamagata., J. Biochem. 96; 1511-1523 (1984), Brzywczy et al., Acta. Biochimica. Polonica. 40(3); 421-428 (1993)), etc., by a known method. Otherwise, commercially available enzymes (for example, o-acetylhomoserine-lyase derived from bacillus genus manufactured by Unitika Ltd.; tradename "GCS", etc.) may be used.

On the other hand, as the enzyme which reacts with cysteine to form hydrogen sulfide, for example, o-acetylserine-lyase, β-cyanoalaninesynthase, cysteine lyase, etc. may preferably be mentioned. o-Acetylserine-lyase is obtainable from microorganisms or plants which are capable of producing it (for example, Burnell et al, Biochim. Biophys. Acta 481; 246-265 (1977), Nagasaw et al., Methods Enzymol 143; 474-478 (1987), Droux et al., Arch. Biochem. Biophys. 295(2); 379-390 (1992), Yamaguchi et al., Biochim. Biophys. Acta 1251; 91-98 (1995)), etc., by a known method. Further, β-cyanoalaninesynthase is obtainable by a method as described in Hendrickson et al., Meth. Enzymol. 17B, 233-239. Cysteine lyase is obtainable by a method as described in Tolasa et al., Biochimiya 31, 98-102 (1966).

Hereinafter, the method for quantitatively determining the reducing substance of the present invention will be explained with reference to preferred embodiments.

For example, when an environmental specimen is used as the measurement specimen, after adding a copper chelating agent to the environmental specimen to a predetermined concentration, and mixing sufficiently, iron (III) ions and a metal indicator specific to iron ions are added thereto, and iron (II) ions formed by reduction with the reducing substance or residual iron (III) ions are reacted with the metal indicator, and then the absorbance is measured for quantitative determination of the reducing substance.

Further, when a biological specimen is used as the measurement specimen, after adding a copper chelating agent and at least one of an aluminum salt and a gallium salt, and preferably further an organic acid thereto and mixing sufficiently, iron (III) ions and a metal indicator specific to iron ions are added thereto, and iron (II) ions formed by reduction with the reducing substance or residual iron (III) ions are reacted with the metal indicator, and then the absorbance is measured for quantitative determination of the reducing substance.

The quantitative determination of the present invention is applicable to the quantitative determination of a sulfur-containing amino acid (homocysteine and cysteine) contained in the biological specimen as mentioned above. Accordingly, in such a case, a hydrogen sulfide-producing enzyme is added together with a copper chelating agent and at least one of an aluminum salt and a gallium salt, and preferably further an organic acid, to form hydrogen sulfide or sulfide ions, followed by quantitative determination. Further, the quantitative determination may be carried out by preliminarily reacting the sulfur-containing amino acid with the hydrogen sulfide-producing enzyme to form hydrogen sulfide or sulfide ions, and then adding a copper chelating agent and at least one of an aluminum salt and a gallium salt, and preferably further an organic acid, followed by quantitative determination.

As mentioned above, the quantitative determination of the present invention is applicable not only to a case where a reducing substance in the specimen is directly quantitatively determined, but also a case where a specific component in the specimen is quantitatively determined by forming a reducing substance from the specific component contained in the specimen, and quantitatively determining the formed reducing substance.

In the quantitative determination of the present invention, the addition concentration (concentration in a reagent) of the copper chelating agent may appropriately be set taking the measurement sensitivity of the reagent, the amount of specimen to be used, etc. into consideration. Usually, it is preferably 0.01 to 50 mM, more preferably 0.1 to 20 mM, particularly preferably 0.5 to 10 mM. Further, the pH, when the copper chelating agent is used, is preferably 4.5 to 9.5, more preferably 6 to 9.

The addition concentration of at least one of the aluminum salt and gallium salt may appropriately be set taking the measurement sensitivity of the reagent, the amount of specimen to be used, etc. into consideration, but it is preferably 0.01 to 10 mM, more preferably 0.05 to 5 mM, particularly preferably 0.1 to 3 mM. Further, the pH, when the at least one of the aluminum salt and gallium salt is used for reaction, is preferably 4.5 to 9.5, more preferably 6 to 9.

The addition concentration of the organic acid may appropriately be set so far as formation of hydroxides of aluminum or gallium in an alkaline pH range can thereby be prevented. Usually, it is preferably 0.01 to 50 mM, more preferably 0.05 to 20 mM, particularly preferably 0.1 to 5 mM.

The addition concentration of the iron (III) ions or the metal indicator specific to iron ions may appropriately be set taking the measurement sensitivity of the reagent, the amount of specimen to be used, etc. into consideration. Usually, the concentration of the iron (III) ions is preferably 0.01 to 50 mM, more preferably 0.1 to 20 mM, particularly preferably 0.5 to 10 mM. Further, the addition concentration of the metal indicator specific to iron ions is preferably 0.01 to 50 mM, more preferably 0.1 to 20 mM, particularly preferably 0.5 to 10 mM. Further, when the iron (III) ions and the metal indicator specific to iron ions are reacted, the pH should preferably be in a range such that iron (II) ions formed by reduction with the reducing substance or residual iron (III) ions, and the metal indicator specific to iron ions easily form a metal chelate complex. For example, it is known that the optimum pH for the formation of a metal chelate complex of the iron (II) ions with "Nitroso-PSAP" (tradename, manufactured by Dojindo Laboratories) is 5.6 to 10.1 (see page 254 of the 22nd catalogue of Dojindo Laboratories).

The addition concentration of the auxiliary agent may appropriately be set depending upon the addition concentration of the iron (III) ions. Usually, it is preferably 0.01 to 10 mM, more preferably 0.05 to 5 mM, particularly preferably 0.1 to 3 mM.

In the quantitative determination of the present invention, in addition to the above components, a surfactant may be added. By adding the surfactant, it is possible to prevent precipitation of reagent components, and improve the reproducibility of measurement. The addition concentration of the surfactant is usually preferably 0.001 to 5%, more preferably 0.01 to 2%.

Then, the reagent for quantitative determination of the present invention will be explained.

The reagent for quantitative determination of the present invention is constituted so that the quantitative determination method of the reducing substance can conveniently be practiced. For example, when the reducing substance in the environmental specimen is quantitatively determined, the reagent for quantitative determination preferably contains at least a copper chelating agent, iron (III) ions and a metal indicator specific to iron ions. Further, when the reducing substance in the biological specimen is quantitatively determined, the reagent for quantitative determination preferably contains at least a copper chelating agent, at least one of an aluminum salt and a gallium salt (preferably further an organic acid), iron (III) ions, and a metal indicator specific to iron ions.

As the above respective basic components, the same ones as explained for the above quantitative determination method may preferably be used. As other components, an auxiliary agent, a buffer solution, a surfactant, etc. may appropriately be used. For example, by using a surfactant, it is possible to prevent precipitation of the reagent components and improve the storage stability of the reagent. Further, when an iron (III) complex is used as the iron (III) ions, the measurement sensitivity can be improved by using an auxiliary agent together. The concentrations of the respective components may appropriately be set on the basis of the above addition concentrations thereof, etc.

The reagent for quantitative determination of the present invention is preferably constituted by at least two reagents. For example, as a reagent system suitable for quantitative determination of a reducing substance in an environmental specimen, a two reagents system comprising a first reagent containing a copper chelating agent and a second reagent containing iron (III) ions and a metal indicator specific to iron ions, may be mentioned. On the other hand, as a reagent system suitable for quantitative determination of a reducing substance in a biological specimen, a two reagents system comprising a first reagent containing a copper chelating agent and at least one of an aluminum salt and a gallium salt, and preferably further an organic acid; and a second reagent containing iron (III) ions and a metal indicator specific to iron ions, may be mentioned. Further, these reagents may contain a surfactant appropriately.

EXAMPLES

Hereinafter, the present invention will be described in further detail with reference to examples.

Example 1

(Study on Influence of Transferrin)
As the specimen and reagent, the following were prepared and used.
Specimen: A 25 µM sodium sulfate aqueous solution having apotransferrin (Apo-Tf, manufactured by Sigma-Aldrich Co.) added so that it would be 0, 1, 2 or 3 mg/mL, was used. As a reagent blank, physiological saline was used.
First reagent:
Tris-HCl buffer solution 110 mM (pH 8.5)
ADA 8.33 mM
thioglycerol 8.33 mM
a surfactant 0.5%
aluminum chloride (or gallium chloride)0.42 mM
IDA (or tartaric acid) 0.42 mM
Here, as the first reagent, 4 types of (1) aluminum chloride/IDA, (2) aluminum chloride/tartaric acid, (3) gallium nitrate/IDA, and (4) gallium nitrate/tartaric acid, were used by combining aluminum chloride or gallium nitrate and IDA or tartaric acid.
Second reagent:
Nitroso-PSAP (manufactured by Dojindo Laboratories) 1 mM
Fe(III) EDTA 5 mM Comparative Example 1

The first reagent of Example 1 was used provided that aluminum chloride, gallium nitrate, IDA and tartaric acid were not used.
The measurement of the specimen was carried out by use of Hitachi 7170 Model Automatic analyzer as follows: Namely, 210 µL of the first reagent was added to 14 µL of the specimen, and incubated at 37° C. for 5 minutes. Further, 56 µL of the second reagent was added thereto, and it was incubated at 37° C. for 5 minutes, and then absorbance at the wavelength of 750 nm was measured. The difference between the measured value and the absorbance when no apotransferrin was added, was converted to a sodium sulfate concentration (µM), and the results are shown in Table 1.

TABLE 1

| Apo-Tf | Example 1 | | | | Comp. |
|---|---|---|---|---|---|
| (mg/mL) | (1) | (2) | (3) | (4) | Ex. 1 |
| 0 | 0 µM | 0 µM | 0 µM | 0 µM | 0 µM |
| 1 | −0.5 µM | −0.2 µM | 0.2 µM | −0.3 µM | −4.7 µM |
| 2 | −1.1 µM | −1.2 µM | −0.8 µM | −1.8 µM | −8.3 µM |
| 3 | −2.5 µM | −1.2 µM | −1.5 µM | −0.9 µM | −11.7 µM |

From Table 1, it is found that clear negative effect is observed corresponding to the addition concentration of apotransferrin in Comparative Example 1, whereas such negative effect is remarkably reduced in the respective conditions ((1) to (4)) in Example 1. From the results, it is also found that the influence of transferrin contained in the specimen can be avoided by adding the aluminum salt or gallium salt.

Example 2

(Study on Influence of Copper)
As the specimen and reagent, the following were prepared and used.
Specimen: A 50 µM sodium sulfate aqueous solution having copper chloride added so that it would be 0, 100 or 200 µg/dL as copper ions, was used.
First reagent:
Tris-HCl buffer solution 110 mM (pH 8.5)
ADA 8.33 mM
thioglycerol 8.33 mM
a surfactant 0.5%
gallium nitrate 0.42 mM
tartaric acid 0.42 mM,
neocuproine hydrochloride (or bathocuproine disulfonate) 1.67 mM
Second reagent:
Nitroso-PSAP (manufactured by Dojindo Laboratories) 1 mM
Fe(III) EDTA 5 mM Comparative Example 2

The first reagent of Example 2 was used provided that neocuproine hydrochloride (or bathocuproine disulfonate) was not used.
Measurement of the specimen was carried out in the same manner as above by use of Hitachi 7170 Model Automatic analyzer. The difference between the measured value and the absorbance when no copper chloride was added, was converted to a sodium sulfate concentration (µM), and the results are shown in Table 2.

TABLE 2

| $Cu^{2+}$ | Example 2 | | Comparative |
|---|---|---|---|
| (µg/dl) | Neocuproine | Bathocuproine | Example 2 |
| 0 | 0 µM | 0 µM | 0 µM |
| 100 | 2.4 µM | 1.6 µM | 72.2 µM |
| 200 | 4.5 µM | 1.7 µM | 94.3 µM |

From Table 2, it is found that positive effect is observed corresponding to the addition concentration of copper chloride in Comparative Example 2, whereas substantially no influence of copper chloride is observed in Example 2. From the results, it is also found that the influence of copper ions contained in the specimen can be avoided by adding the neocuproine hydrochloride or bathocuproine disulfonate.

Example 3

(Study on Influence of Transferrin)
Specimen: A L-homocystine (manufactured by Sigma-Aldrich Co.) 12.5 µM aqueous solution (corresponds to 25 µM as L-homocysteine) having apotransferrin added so that it would be 0, 1, 2 or 3 mg/mL was used.
First reagent:
Tris-HCl buffer solution 110 mM (pH 8.5)
ADA 8.33 mM thioglycerol 8.33 mM a surfactant 0.5% gallium nitrate 0.42 mM tartaric acid 0.42 mM neocuproine hydrochloride (or bathocuproine disulfonate) 1.67 mM recombinant o-acetylhomoserine-lyase (tradename "rGCS", manufactured by Unitika Ltd.) 2.5 U/mL (the volume activity is the indicated value of the manufacturer)

Second reagent:

Nitroso-PSAP (manufactured by Dojindo Laboratories) 1 mM

Fe (III) EDTA 5 mM

Comparative Example 3

The first reagent of Example 3 was used provided that the gallium nitrate and tartaric acid were not used.

Measurement of the specimen was carried out in the same manner as above by use of Hitachi 7170 Model Automatic analyzer. The difference between the measured value and the absorbance when no apotransferrin was added, was converted to L-homocysteine concentration ($\mu M$), and the results are shown in Table 3.

TABLE 3

| Apo-Tf (mg/mL) | Example 3 | Comp. Ex. 3 |
| --- | --- | --- |
| 0 | 0 $\mu M$ | 0 $\mu M$ |
| 1 | 0.2 $\mu M$ | −3.3 $\mu M$ |
| 2 | −1.1 $\mu M$ | −4.2 $\mu M$ |
| 3 | −1.3 $\mu M$ | −4.6 $\mu M$ |

From Table 3, it is found that as compared with Comparative Example 3, the negative effect of transferrin was reduced in Example 3 wherein the gallium salt was added.

Example 4

(Study on Influence of serum Copper)

Specimen: L-homocystine 12.5 $\mu M$ aqueous solution (corresponds to 25 $\mu M$ as L-homocysteine) having ceruloplasmin (manufactured by Sigma-Aldrich Co.) which is a type of serum protein and to which 90 to 95% of copper in serum are bound, added so that it would be 0, 4.6, 9.3, 18.5 or 37.0 mg/dL, was used. Here, in the lot of the ceruloplasmin used, 88.8 mg protein corresponds to 133 $\mu g$ copper.

As the first and second reagents, the same ones as in Example 3 were used.

Comparative Example 4

As the first and second reagents, the same ones as in Comparative Example 3 were used.

Measurement of the specimen was carried out in the same manner as above by use of Hitachi 7170 Model Automatic analyzer. The difference between the measured value and the absorbance when no ceruloplasmin was added, was converted to L-homocysteine concentration ($\mu M$), and the results are shown in Table 4.

TABLE 4

| Ceruloplasmin (mg/mL) | Example 4 | Comp. Ex. 4 |
| --- | --- | --- |
| 0 | 0 $\mu M$ | 0 $\mu M$ |
| 4.6 | 0.4 $\mu M$ | 2.3 $\mu M$ |
| 9.3 | 0.2 $\mu M$ | 5.1 $\mu M$ |
| 18.5 | 0.8 $\mu M$ | 9.8 $\mu M$ |
| 37.0 | 1.1 $\mu M$ | 18.6 $\mu M$ |

From Table 4, it is found that positive effect is observed corresponding to the concentration of ceruloplasmin. On the other hand, in Example 4, substantially no influence of ceruloplasmin is observed. From the results, it is also found that the influence of serum copper can be avoided by adding neocuproine.

According to the method for quantitatively determining a reducing substance in a specimen of the present invention which comprises reacting a reducing substance in a test specimen with iron (III) ions, reacting iron (II) ions thereby formed or residual iron (III) ions with a metal indicator which is specific to these iron ions to undergo color development, and carrying out quantitative determination by measuring the degree of color development, wherein a copper chelating agent and, preferably, further at least one of an aluminum salt and a gallium salt are added to the specimen before the reaction of the reducing substance with the iron (III) ions, it is possible to avoid the influence of other components in the specimen and quantitatively determine the reducing substance accurately.

What is claimed is:

1. A method for quantitatively determining a reducing substance, which comprises, in order:

adding a chelating agent which is specific to copper ions, and at least one of an aluminum salt and a gallium salt, to a test specimen, reacting a reducing substance in the test specimen with iron (III) ions thereby forming iron (II) ions, reacting said iron (II) ions or residual iron (III) ions with a metal indicator which is capable of reacting specifically with the iron (II) ions or the residual iron (III) ions to undergo color development, and carrying out quantitative determination by measuring the degree of color development.

2. The method for quantitatively determining a reducing substance according to claim 1, wherein the chelating agent specific to the copper ions is at least one selected from the group consisting of neocuproine, bathocuproine and salts thereof.

3. The method for quantitatively determining a reducing substance according to claim 1, further comprising adding an organic acid to the test specimen together with the at least one of an aluminum salt and a gallium salt.

4. The method for quantitatively determining a reducing substance according to claim 3, wherein the organic acid is tartaric acid.

5. The method for quantitatively determining a reducing substance according to claim 1, wherein the reducing substance is hydrogen sulfide or sulfide ions.

6. The method for quantitatively determining a reducing substance according to claim 5, wherein the hydrogen sulfide or sulfide ions are formed by reacting a sulfur-containing amino acid contained in the test specimen with an enzyme which is capable of reacting with the sulfur-containing amino acid to form hydrogen sulfide.

7. The method for quantitatively determining a reducing substance according to claim 1, wherein the iron (III) ions constitute a complex.

8. The method for quantitatively determining a reducing substance according to claim 7, further comprising adding an auxiliary agent, which has an ability of coordinating ligands around the iron ions, to the test specimen together with the complex of the iron (III) ions.

9. The method for quantitatively determining a reducing substance according to claim 1, wherein the test specimen is a biological specimen or an environmental specimen.

10. A reagent for quantitative determination of a reducing substance, which comprises a chelating agent which is specific to copper ions, at least one of an aluminum salt and a gallium salt, iron (III) ions, and a metal indicator which is capable of reacting specifically with iron (II) ions or iron (III) ions to undergo color development.

11. The reagent for quantitative determination of a reducing substance according to claim 10, wherein the chelating agent which is specific to the copper ions is at least one selected from the group consisting of neocuproine, bathocuproine and salts thereof.

12. The reagent for quantitative determination of a reducing substance according to claim 10, which further comprises an organic acid.

13. The reagent for quantitative determination of a reducing substance according to claim 12, wherein the organic acid is tartaric acid.

14. The reagent for quantitative determination of a reducing substance according to claim 10, which further comprises an enzyme which is capable of reacting with a sulfur-containing amino acid to form hydrogen sulfide.

15. The reagent for quantitative determination of a reducing substance according to claim 10, wherein the iron (III) ions constitute a complex.

16. The reagent for quantitative determination of a reducing substance according to claim 15, which further comprises an auxiliary agent which has an ability of coordinating ligands around the iron ions.

17. The reagent for quantitative determination of a reducing substance according to claim 10, which comprises a first reagent comprising the copper chelating agent and the at least one of an aluminum salt and a gallium salt, and a second reagent comprising the iron (III) ions and the metal indicator.

* * * * *